(12) United States Patent
Miao et al.

(10) Patent No.: US 12,246,348 B2
(45) Date of Patent: Mar. 11, 2025

(54) CAPACITIVE MICROMACHINED ULTRASONIC TRANSDUCERS (CMUTs) HAVING NON-UNIFORM PEDESTALS

(71) Applicant: BFLY OPERATIONS, INC., Burlington, MA (US)

(72) Inventors: Lingyun Miao, Fremont, CA (US); Sarp Satir, San Francisco, CA (US)

(73) Assignee: BFLY Operations, Inc, Burlington, MA (US)

( * ) Notice: Subject to any disclaimer, the term of this patent is extended or adjusted under 35 U.S.C. 154(b) by 226 days.

(21) Appl. No.: 17/686,045

(22) Filed: Mar. 3, 2022

(65) Prior Publication Data

US 2022/0283121 A1 Sep. 8, 2022

Related U.S. Application Data

(60) Provisional application No. 63/156,906, filed on Mar. 4, 2021.

(51) Int. Cl.
*B06B 1/02* (2006.01)
*G01N 29/24* (2006.01)

(52) U.S. Cl.
CPC ....... *B06B 1/0292* (2013.01); *G01N 29/2406* (2013.01); *G01N 2291/106* (2013.01)

(58) Field of Classification Search
None
See application file for complete search history.

(56) References Cited

U.S. PATENT DOCUMENTS

| 5,619,476 | A | 4/1997 | Haller et al. |
| 5,894,452 | A | 4/1999 | Ladabaum et al. |
| 5,982,709 | A | 11/1999 | Ladabaum et al. |
| 6,004,832 | A | 12/1999 | Haller et al. |
| 6,262,946 | B1 | 7/2001 | Khuri-Yakub et al. |
| 6,430,109 | B1 | 8/2002 | Khuri-Yakub et al. |
| 6,571,445 | B2 * | 6/2003 | Ladabaum ............ B06B 1/0292 29/609.1 |
| 6,836,020 | B2 | 12/2004 | Cheng et al. |
| 6,958,255 | B2 | 10/2005 | Khuri et al. |

(Continued)

FOREIGN PATENT DOCUMENTS

CN 101977026 A 2/2011
CN 105307975 A 2/2016
(Continued)

OTHER PUBLICATIONS

Extended European Search Report dated Jul. 11, 2022 in connection with European Application No. 19884050.6.
(Continued)

*Primary Examiner* — Isam A Alsomiri
*Assistant Examiner* — Jonathan D Armstrong
(74) *Attorney, Agent, or Firm* — Boston & Galway, LLC

(57) ABSTRACT

An ultrasound device is described. The ultrasound device comprises a capacitive micromachined ultrasonic transducer (CMUT). The CMUT comprises a membrane, a substrate, a cavity disposed between the membrane and the substrate, wherein the cavity comprises a bottom surface adjacent to the substrate, and non-uniform pedestals protruding from the bottom surface of the cavity into the cavity and towards the membrane.

11 Claims, 11 Drawing Sheets

(56) References Cited

U.S. PATENT DOCUMENTS

| | | | |
|---|---|---|---|
| 7,274,623 B2 | 9/2007 | Bayram et al. | |
| 7,321,181 B2 | 1/2008 | Khuri et al. | |
| 7,530,952 B2* | 5/2009 | Huang | B06B 1/0292 367/181 |
| 7,545,075 B2 | 6/2009 | Huang et al. | |
| 7,615,834 B2 | 11/2009 | Khuri-Yakub et al. | |
| 7,741,686 B2 | 6/2010 | Khuri et al. | |
| 7,745,248 B2 | 6/2010 | Park et al. | |
| 7,745,973 B2 | 6/2010 | Bayram et al. | |
| 7,846,102 B2 | 12/2010 | Kupnik et al. | |
| 7,972,271 B2 | 7/2011 | Johnson et al. | |
| 8,008,105 B2* | 8/2011 | Huang | B06B 1/0292 438/52 |
| 8,276,433 B2 | 10/2012 | Kupnik et al. | |
| 8,402,831 B2 | 3/2013 | Kupnik et al. | |
| 8,451,693 B2 | 5/2013 | Nikoozadeh et al. | |
| 9,067,779 B1 | 6/2015 | Rothberg et al. | |
| 9,249,008 B2* | 2/2016 | Hsu | G01L 9/0073 |
| 9,499,392 B2 | 11/2016 | Rothberg et al. | |
| 9,505,030 B2 | 11/2016 | Rothberg et al. | |
| 9,533,873 B2 | 1/2017 | Rothberg et al. | |
| 10,512,936 B2 | 12/2019 | Alie et al. | |
| 10,525,506 B2 | 1/2020 | Alie et al. | |
| 10,856,840 B2 | 12/2020 | Rothberg et al. | |
| 10,939,214 B2* | 3/2021 | Kuntzman | H04R 7/12 |
| 11,617,042 B2* | 3/2023 | Kuntzman | H04R 19/04 381/174 |
| 2003/0220554 A1 | 11/2003 | Grenon et al. | |
| 2005/0228285 A1 | 10/2005 | Huang et al. | |
| 2006/0004289 A1 | 1/2006 | Tian et al. | |
| 2006/0075818 A1 | 4/2006 | Huang et al. | |
| 2007/0059858 A1 | 3/2007 | Caronti et al. | |
| 2007/0164632 A1 | 7/2007 | Adachi et al. | |
| 2007/0215964 A1 | 9/2007 | Khuri-Yakub et al. | |
| 2009/0122651 A1 | 5/2009 | Kupnik et al. | |
| 2009/0142872 A1 | 6/2009 | Park et al. | |
| 2010/0173437 A1* | 7/2010 | Wygant | B06B 1/0292 257/E21.214 |
| 2010/0202254 A1 | 8/2010 | Roest et al. | |
| 2010/0225200 A1 | 9/2010 | Kupnik et al. | |
| 2011/0050033 A1 | 3/2011 | Nikoozadeh et al. | |
| 2011/0055447 A1 | 3/2011 | Costa | |
| 2011/0241802 A1* | 10/2011 | Joshi | H01P 7/06 333/209 |
| 2012/0243095 A1 | 9/2012 | Sagberg et al. | |
| 2013/0087867 A1 | 4/2013 | Ho et al. | |
| 2013/0135971 A1 | 5/2013 | Nakanishi | |
| 2014/0217478 A1 | 8/2014 | Rothberg et al. | |
| 2014/0219062 A1 | 8/2014 | Rothberg et al. | |
| 2014/0265720 A1 | 9/2014 | El-Gamal et al. | |
| 2015/0145374 A1 | 5/2015 | Xu et al. | |
| 2015/0368097 A1 | 12/2015 | Behrendt et al. | |
| 2016/0009544 A1 | 1/2016 | Rothberg et al. | |
| 2016/0290970 A1 | 10/2016 | Rothberg et al. | |
| 2016/0318753 A1 | 11/2016 | Chou | |
| 2016/0337761 A1* | 11/2016 | Hall | G01S 3/801 |
| 2016/0379973 A1 | 12/2016 | Rothberg et al. | |
| 2017/0360399 A1 | 12/2017 | Rothberg et al. | |
| 2018/0243792 A1 | 8/2018 | Rothberg et al. | |
| 2019/0000422 A1 | 1/2019 | West et al. | |
| 2019/0055117 A1 | 2/2019 | Steiert | |
| 2019/0231312 A1 | 8/2019 | Fife et al. | |
| 2019/0275561 A1 | 9/2019 | Fife et al. | |
| 2019/0336099 A1 | 11/2019 | Fife et al. | |
| 2019/0336103 A1 | 11/2019 | Fife et al. | |
| 2019/0336104 A1 | 11/2019 | Fife et al. | |
| 2020/0013691 A1 | 1/2020 | Liu et al. | |
| 2020/0093463 A1 | 3/2020 | Sams et al. | |
| 2020/0102214 A1 | 4/2020 | Liu et al. | |
| 2020/0147641 A1 | 5/2020 | Fife et al. | |
| 2020/0156110 A1 | 5/2020 | Miao et al. | |
| 2020/0156111 A1* | 5/2020 | Gross | B81B 3/0086 |
| 2020/0163654 A1 | 5/2020 | Satir et al. | |
| 2020/0184177 A1 | 6/2020 | Liu et al. | |
| 2020/0254487 A1 | 8/2020 | Miao et al. | |
| 2020/0269279 A1 | 8/2020 | Miao et al. | |
| 2020/0324318 A1 | 10/2020 | Liu et al. | |
| 2020/0324319 A1 | 10/2020 | Miao et al. | |
| 2020/0384503 A1 | 12/2020 | Schmid et al. | |
| 2020/0407220 A1 | 12/2020 | Lin et al. | |
| 2021/0038193 A1 | 2/2021 | Liu et al. | |
| 2021/0285917 A1 | 9/2021 | Liu et al. | |
| 2021/0361260 A1 | 11/2021 | Miao et al. | |
| 2022/0280972 A1 | 9/2022 | Liu et al. | |
| 2022/0283121 A1* | 9/2022 | Miao | G01N 29/2406 |
| 2023/0278073 A1* | 9/2023 | Lien | B06B 1/0292 310/309 |

FOREIGN PATENT DOCUMENTS

| | | |
|---|---|---|
| CN | 109092650 A | 12/2018 |
| WO | WO 01/97562 A2 | 12/2001 |

OTHER PUBLICATIONS

International Search Report and Written Opinion mailed Jan. 29, 2020 in connection with International Application No. PCT/US2019/061403.

International Preliminary Report on Patentability mailed May 27, 2021 in connection with International Application No. PCT/US2019/061403.

Invitation to Pay Additional Fees mailed Jan. 13, 2020 in connection with International Application No. PCT/US2019/061419.

International Search Report and Written Opinion mailed Mar. 10, 2020 in connection with International Application No. PCT/US2019/061419.

International Preliminary Report on Patentability mailed Sep. 2, 2021 for International Application No. PCT/US2019/061419.

Invitation to Pay Additional Fees mailed Jul. 5, 2022 in connection with International Application No. PCT/US2022/018680.

International Search Report and Written Opinion mailed Sep. 6, 2022 in connection with International Application No. PCT/US2022/018680.

International Search Report and Written Opinion mailed Jun. 2, 2022 in connection with International Application No. PCT/US2022/018701.

Khuri-Yakub et al., Capacitive micromachined ultrasonic transducers for medical imaging and therapy. J. Micromech and Microeng. Apr. 28, 2011; 21(5):054004. 11 pages.

Khuri-Yakub et al., Miniaturized Ultrasound Imaging Probes Enabled by CMUT Arrays with Integrated Frontend Electronic Circuits. Annual International Conference of the IEEE Engineering in Medicine and Biology 2010, 13 pages.

Kupnik et al., Wafer-bonded CMUT meets CMOS MEMS-based Ultrasonic Transducer Arrays including Electronics Integration. CMOS Emerging Technology Workshop, Whistler, Canada. May 21, 2010; 22 pages.

Kupnik et al., CMUT Fabrication Based On A Thick Buried Oxide Layer. IEEE International Ultrasonics Symposium Oct. 11, 2010; pp. 547-550.

* cited by examiner

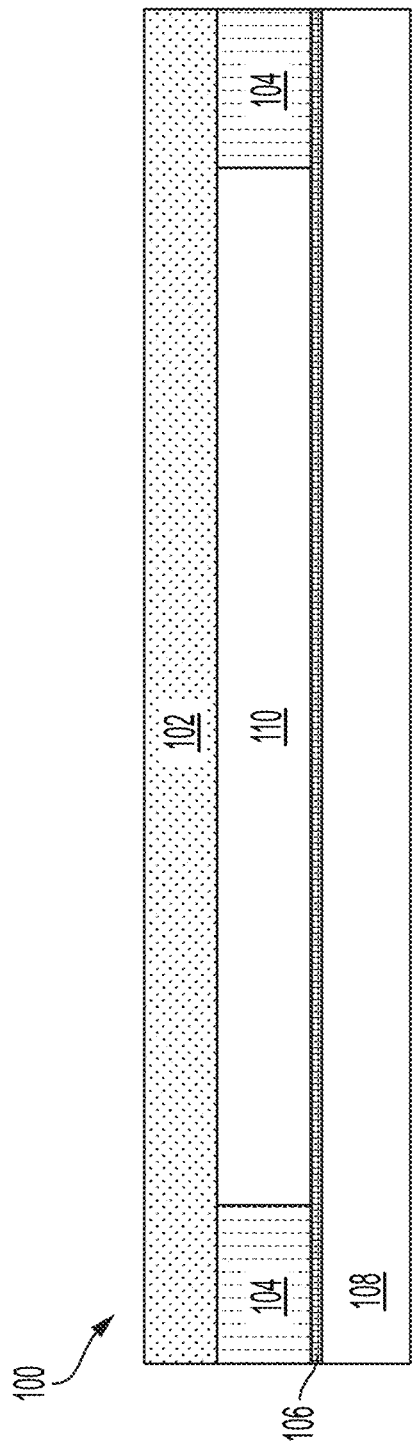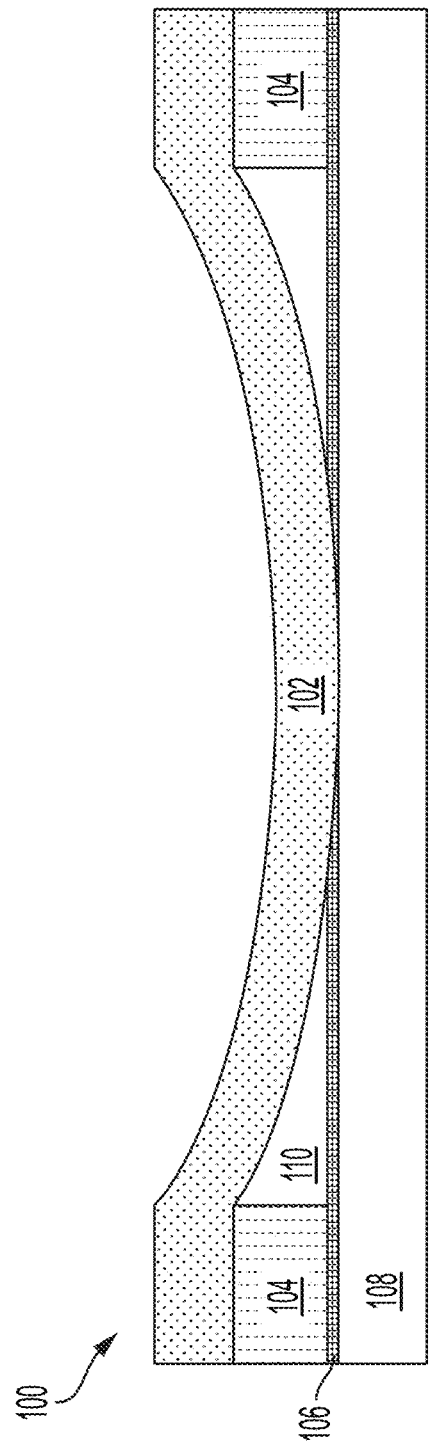

CAPACITIVE MICROMACHINED ULTRASONIC TRANSDUCERS (CMUTs) HAVING NON-UNIFORM PEDESTALS

CROSS-REFERENCE TO RELATED APPLICATIONS

The present application claims the benefit under 35 U.S.C. § 119(e) of U.S. Provisional Application Ser. No. 63/156,906, filed Mar. 4, 2021, entitled "CAPACITIVE MICROMACHINED ULTRASONIC TRANSDUCERS (CMUTs) HAVING NON-UNIFORM PEDESTALS," which is hereby incorporated by reference herein in its entirety.

FIELD

The present disclosure relates to capacitive micromachined ultrasonic transducers (CMUTs), and more specifically to CMUTs having non-uniform pedestals.

BACKGROUND

Ultrasound devices may be used to perform diagnostic imaging and/or treatment, using sound waves with frequencies that are higher than those audible to humans. Ultrasound imaging may be used to see internal soft tissue body structures. When pulses of ultrasound are transmitted into tissue, sound waves of different amplitudes may be reflected back towards the probe at different tissue interfaces. These reflected sound waves may then be recorded and displayed as an image to the operator. The strength (amplitude) of the sound signal and the time it takes for the wave to travel through the body may provide information used to produce the ultrasound image. Many different types of images can be formed using ultrasound devices. For example, images can be generated that show two-dimensional cross-sections of tissue, blood flow, motion of tissue over time, the location of blood, the presence of specific molecules, the stiffness of tissue, or the anatomy of a three-dimensional region.

SUMMARY

An ultrasound device is described. The ultrasound device comprises a capacitive micromachined ultrasonic transducer (CMUT).

In some aspects, the techniques described herein relate to an ultrasound device, including: a capacitive micromachined ultrasonic transducer (CMUT), including: a substrate; a membrane coupled to the substrate such that a cavity exists between the substrate and the membrane; a cavity bottom layer adjacent to the substrate; and non-uniform pedestals protruding from the cavity bottom layer into the cavity and towards the membrane, wherein the non-uniform pedestals include first non-uniform pedestals having a first pedestal diameter, $d_1$, and second non-uniform pedestals having a second pedestal diameter, $d_2$, different than $d_1$, and the cavity bottom layer includes: a first region having a first radius, the first region including the first non-uniform pedestals; and a second region having a first inner radius and a first outer radius, the first inner radius being approximately equal to the first radius and the first outer radius being greater than the first inner radius, the second region including the second non-uniform pedestals.

In some embodiments, $d_1$ is greater than $d_2$.

In some embodiments, each adjacent pair of the first non-uniform pedestals has a pitch, $L_1$, each adjacent pair of the second non-uniform pedestals has a pitch, $L_2$, and $L_1$ has a different value than $L_2$.

In some embodiments, $L_1$ is greater than $L_2$.

In some embodiments, the non-uniform pedestals further include third non-uniform pedestals having a third pedestal diameter, $d_3$, and the cavity bottom layer further includes a third region having a second inner radius and a second outer radius, the second inner radius being approximately equal to the first outer radius and the second outer radius being greater than the second inner radius, the second region including the third non-uniform pedestals.

In some embodiments, $d_3$ has a different value than $d_1$ and $d_2$.

In some embodiments, $d_3$ is greater than $d_2$ and less than $d_1$.

In some embodiments, each adjacent pair of the third non-uniform pedestals has a pitch $L_3$, and $L_3$ has a different value than $L_1$ and $L_2$.

In some embodiments, $L_1$ is greater than $L_3$.

In some embodiments, $L_2$ is greater than or approximately equal to $L_3$.

In some embodiments, each of the non-uniform pedestals has a height that is in a range from 20 nanometers to 100 nanometers above the bottom surface of the cavity.

In some aspects, the techniques described herein relate to an ultrasound device, including: a capacitive micromachined ultrasonic transducer (CMUT), including: a substrate; a membrane coupled to the substrate such that a cavity exists between the substrate and the membrane; a cavity bottom layer adjacent to the substrate; and non-uniform pedestals protruding from the cavity bottom layer into the cavity and towards the membrane, wherein: the non-uniform pedestals include first pedestals and second pedestals; the first pedestals have a first characteristic, and the second pedestals have a second characteristic; and the first and second characteristics have different values.

In some embodiments, each of the non-uniform pedestals has a top surface facing the membrane and having a top surface area; the first characteristic includes an average value of the top surface area of each of the first pedestals and the second characteristic includes an average value of the top surface area of each of the second pedestals.

In some embodiments, each adjacent pair of the first and second pedestals has a pitch; and the first characteristic includes an average value of the pitch of each adjacent pair of the first pedestals and the second characteristic includes an average value of the pitch of each adjacent pair of the second pedestals.

In some embodiments, the first pedestals protrude are disposed in an inner region of the bottom surface of the cavity; and the second pedestals are disposed in an outer region of the bottom surface of the cavity.

In some embodiments, an average value of a distance of each of the first pedestals from a centroid of the bottom surface of the cavity is less than an average value of the distance of each of the second pedestals from the centroid of the bottom surface of the cavity.

In some embodiments, the inner region is approximately a circle in shape, is approximately centered at a centroid of the bottom surface of the cavity and has a radius $R_1$; the outer region is approximately an annular ring in shape, is approximately centered at the centroid of the bottom surface of the cavity and has an inner radius $R_1$ and an outer radius $R_2$; and $R_1$ is less than $R_2$.

In some embodiments, the non-uniform pedestals include first pedestals, second pedestals, and third pedestals; the first pedestals have a first characteristic, the second pedestals have a second characteristic, and the third pedestals have a third characteristic; and the first characteristic has a different value than the second characteristic and/or the first characteristic has a different value than the third characteristic and/or the second characteristic has a different value than the third characteristic.

In some embodiments, each of the non-uniform pedestals has a height that is in a range from 20 nanometers to 100 nanometers above the bottom surface of the cavity.

In some aspects, the techniques described herein relate to a method of forming an ultrasound device, including: forming a capacitive micromachined ultrasonic transducer (CMUT) by: forming a first layer on a substrate; patterning the first layer on the substrate; forming a second layer on the first layer such that the pattern of the first layer defines non-uniform pedestals in the second layer; and forming a membrane over the substrate such that a cavity exists between the non-uniform pedestals and the membrane.

BRIEF DESCRIPTION OF THE DRAWINGS

The following brief description of the drawings is meant to assist the understanding of one skilled in the art and is not meant to unduly limit any present or future claims relating to the present disclosure. Various aspects and embodiments are described with reference to the following exemplary and non-limiting figures. It should be appreciated by one skilled in the art that the figures are not necessarily drawn to scale. Items appearing in multiple figures are indicated by the same or a similar reference number in all the figures in which they appear.

FIG. 1 illustrates a side view of a capacitive micromachined ultrasonic transducer (CMUT) in a non-collapsed position.

FIG. 2 illustrates a side view of the CMUT of FIG. 1 in a collapsed position.

DETAILED DESCRIPTION

Figure 3:
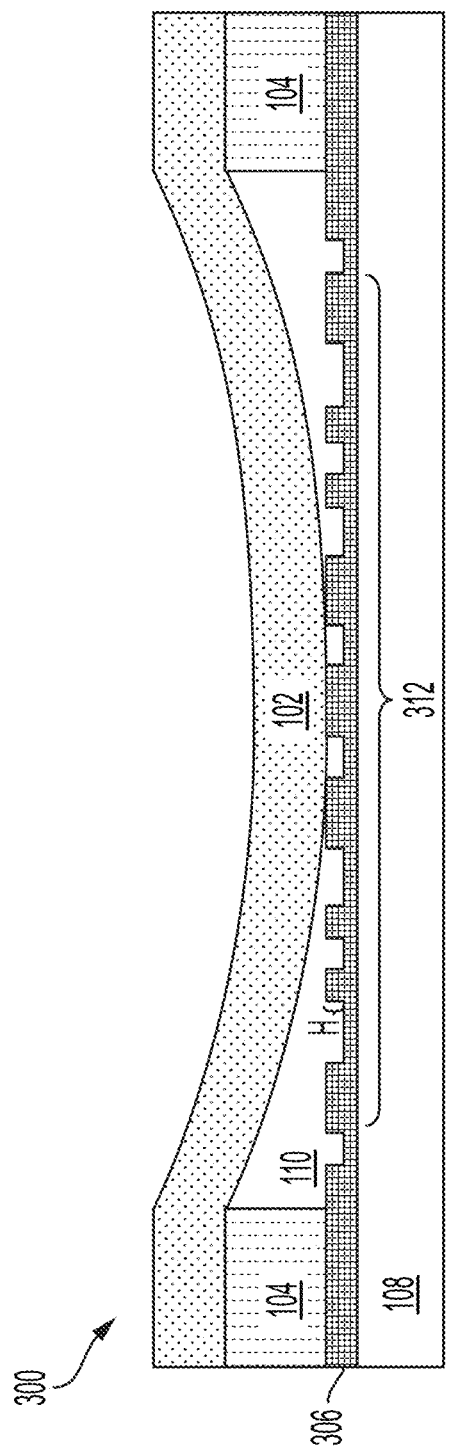
FIG. 3 illustrates a side view of another CMUT that includes non-uniform pedestals, in accordance with certain embodiments described herein.

Capacitive micromachined ultrasonic transducers (CMUTs) may include a membrane, a substrate, and a cavity in between. In operation, the membrane may vibrate up and down in response to a time-varying voltage applied across the cavity, between the membrane and the substrate, thus varying the cavity height. This vibration of the membrane may cause transmission of ultrasound waves. In addition, in response to reception of ultrasound waves, the membrane may vibrate up and down, thereby varying the cavity height and generating a time-varying voltage across the cavity (i.e., between the membrane and the substrate) which can be detected. In some operating modes of transmission or reception of ultrasound waves, the membrane may move into a collapsed position in which the membrane contacts the bottom layer of the cavity. It may be desirable for the membrane to return to a non-collapsed position after transmission or reception of ultrasound waves. However, due to various mechanisms such as surface charging or surface energy, the membrane may remain stuck to the cavity bottom layer, a phenomenon that may be referred to as membrane stiction. Membrane stiction may be undesirable as it may result in the CMUT operating poorly or ceasing to operate.

Generally, pedestals protruding from the bottom layer of a cavity may be helpful in reducing membrane stiction due to reduction of the contact area between the membrane and the cavity bottom layer. The inventors have recognized that non-uniform pedestals may improve operation and/or device reliability such as longevity of a CMUT. A CMUT may be said to have non-uniform pedestals where a subset (i.e., one or more, but fewer than all) of the pedestals has at least one characteristic that is different than another subset of the pedestals. For example, a subset of the pedestals may have a different top surface area than that of another subset of the pedestals. As another example, a subset of the pedestals may have a pitch that is different than that of another subset of the pedestals. In some embodiments, a CMUT may have one subset of pedestals that differs from another subset of pedestals of the CMUT in both the top surface area and the pitch of the pedestals. In general, the inventors have recognized that, in certain regions of a CMUT, pedestals having a certain characteristic may be helpful, while in other regions of a CMUT, pedestals having a different characteristic may be helpful. This may be because in certain regions of a CMUT, certain factors relevant to operation and/or device reliability of a CMUT, such as stiction, sensing sensitivity, and/or impact force, may be more important, and certain characteristics of pedestals may be more helpful in relation to those factors.

Various aspects of the present disclosure may be used alone, in combination, or in a variety of arrangements not explicit in the embodiments described in the foregoing and is therefore not limited in its application to the details and arrangement of components set forth in the foregoing description or illustrated in the drawings. For example, aspects described in one embodiment may be combined in any manner with aspects described in other embodiments.

FIG. 1 illustrates a side view of a CMUT 100 in a non-collapsed position. The CMUT includes a membrane 102, sidewalls 104, a cavity bottom layer 106, a substrate 108, and a cavity 110. The cavity 110 is disposed between the membrane 102 and the cavity bottom layer 106. The sidewalls 104 are also disposed between the membrane 102 and the cavity bottom layer 106 at the perimeter of the cavity 110. The cavity bottom layer 106 is disposed on the substrate 108, which is on the opposite side of the cavity bottom layer 106 as the cavity 110. The cavity bottom layer 106 (and any other cavity bottom layers described herein) may be considered the bottom surface of the cavity 110. In some embodiments, the substrate 108 may include multiple layers, such as a metal sensing layer. The cavity bottom layer 106 (and any other cavity bottom layer described herein) may be considered adjacent to the substrate 108 in that the cavity bottom layer 106 is on the same side of the cavity 110 as the substrate 108, rather than being on the same side of the cavity 110 as the membrane 102.

In operation, the membrane 102 may vibrate up and down in response to a time-varying voltage applied across the cavity 110 (i.e., between the membrane 102 and the substrate 108), thus varying a height of the cavity. This vibration of the membrane 102 may cause transmission of ultrasound waves. In addition, in response to reception of ultrasound waves, the membrane 102 may vibrate up and down, thereby generating a time-varying voltage across the cavity 110 (i.e., between the membrane 102 and the substrate 108) which can be detected. Prior to transmission or reception of ultrasound waves, the membrane 102 may be in the non-collapsed position illustrated in FIG. 1. In the non-collapsed position, the membrane 102 does not contact the cavity bottom layer 106.

FIG. 2 illustrates a side view of the CMUT 100 in a collapsed position. During transmission or reception of ultrasound waves, the membrane 102 may move into the collapsed position illustrated in FIG. 2, in which the membrane 102 has moved down sufficiently far that it contacts the cavity bottom layer 106. It may be desirable for the membrane 102 to return to the non-collapsed position illustrated in FIG. 1 after transmission or reception of ultrasound waves. However, due to various mechanisms such as surface charging or surface energy, the membrane 102 may remain stuck to the cavity bottom layer 106, a phenomenon that may be referred to as membrane stiction. Membrane stiction may be undesirable as it may result in the CMUT 100 operating poorly or ceasing to operate.

FIG. 3 illustrates a side view of another CMUT 300 that includes non-uniform pedestals, in accordance with certain embodiments described herein. The CMUT 300 is the same as the CMUT 100 except that the CMUT 300 includes a cavity bottom layer 306, which differs from the cavity bottom layer 106, and non-uniform pedestals 312 protruding from the cavity bottom layer 306 into the cavity 110 and towards the membrane 102.

Pedestals 312 may be helpful in reducing membrane stiction due to a reduction of the contact area between the membrane 102 and the cavity bottom layer. For example, the contact area between membrane 102 and cavity bottom layer 306 in FIG. 3 will be less than that between membrane 102 and cavity bottom layer 106 due to the cavity bottom layer 306 having a non-uniform surface in the form of non-uniform pedestals 312, presuming all other dimensions, materials, and operating conditions of the CMUTs 100 and 300 are the same as each other.

The pedestals described herein may be understood to be larger in height than the surface roughness of the cavity bottom layer (e.g., cavity bottom layer 306) itself. In some embodiments, the difference in height between the pedestals and the surface roughness of the cavity bottom layer may be more than 10 times greater than the surface roughness of the cavity bottom layer. In some embodiments, the pedestals may protrude from the cavity bottom layer and have a height H above a surface of the cavity bottom layer that is at least 20 nanometers (nm), at least 25 nm, or at least 30 nm. In some embodiments, the pedestals may protrude from the cavity bottom layer and have a height H above a surface of the cavity bottom layer that is in a range from 20 nm to 100 nm.

The non-uniform pedestals 312 may include a subset (i.e., one or more, but fewer than all) of pedestals having at least one characteristic that is different than another subset of the non-uniform pedestals 312. In some embodiments, a subset of the non-uniform pedestals 312 may have a different top surface area than that of another subset of the non-uniform pedestals 312. Top surface area refers to the area of the top surface of the pedestal, namely the surface facing the membrane 102. As another example, a subset of the non-uniform pedestals 312 may be separated by a pitch that is different than that separating another subset of the non-uniform pedestals 312. Pitch may be determined as the distance between the centroids of the top surfaces of two adjacent pedestals. In some embodiments, more than two subsets of the non-uniform pedestals 312 may have different characteristics. In some embodiments, each of three, four, five, or six subsets may have different characteristics than the other subsets. In some embodiments, a subset (i.e., one or more, but fewer than all) of the non-uniform pedestals 312 may have two or more characteristics (e.g., two, three, four, five, or six) that are different than those characteristics of another subset of the non-uniform pedestals 312.

In some embodiments, two subsets of the non-uniform pedestals 312 may be considered to have different characteristics when, for a certain quantifiable property of the non-uniform pedestals 312, the average value of that property among all pedestals in one subset is different than the average value of that property among all pedestals in the other subset. As one example, two subsets of the non-uniform pedestals 312 may have different top surface areas if the average value of the top surface area of each of the pedestals in the first subset is different than the average value of the top surface area of each of the pedestals in the second subset. As another example, two subsets of the non-uniform pedestals 312 may have different pitches if the average value of the pitch between adjacent pairs of pedestals in the first subset is different than the average value of the pitch between adjacent pairs of pedestals in the second subset.

In some embodiments, a first average value may be considered to be different than a second average value when the first average value is different from the second average value by a threshold percentage of the second average value. For example, in those embodiments in which the average top surface area of a first subset of the pedestals differs from the average surface area of a second subset of the pedestals, the threshold percentage may be in a range from 5% to 400%, in a range from 50% to 200%, or in a range from 80% to 120%, including any value or range of values within these ranges. As another example, in those embodiments in which the average diameter of a first subset of the pedestals differs from the average diameter of a second subset of the pedestals, the threshold percentage may be in a range from 1% to 100%, in a range from 5% to 50%, or in a range from 20% to 40%, including any value or range of values within these ranges. As another example, in those embodiments in which the average pitch of a first subset of the pedestals differs from the average pitch of a second subset of the pedestals, the threshold percentage may be in a range from 1% to 200%, in a range from 5% to 150%, or in a range from 80% to 120%, including any value or range of values within these ranges.

In some embodiments, the average values of the characteristics of the non-uniform pedestals 312 may depend on the positions of the non-uniform pedestals 312. A first subset of the non-uniform pedestals 312 at certain positions may have one average value of one or more characteristics (e.g., a certain top surface area, diameter, and/or a certain pitch) and a second subset of the non-uniform pedestals 312 at different positions may have a different average value of one or more characteristics (e.g., a different top surface area, diameter, and/or a different pitch). The different positions may be, for example, within different regions of the cavity bottom layer 306. As a further example, the average values of the characteristics of subsets of the non-uniform pedestals 312 may depend on the relative positioning of the subsets along a radius of the cavity. For example, a first subset of pedestals may be in an inner region of a cavity bottom layer and a second subset of pedestals may be in an outer region of the cavity bottom layer when the average value of the distance of each pedestal in the first group from the centroid of the cavity bottom layer is less than the average value of the distance of each pedestal in the second group from the centroid of the bottom surface of the cavity The inventors have recognized that non-uniform pedestals may be helpful in improving operation and/or device reliability such as longevity of a CMUT. For example, the inventors have recognized that, in certain regions of a CMUT, pedestals having a certain characteristic may be helpful, while in other regions of a CMUT, pedestals having different characteristics may be helpful, since the importance of stiction, sensing sensitivity, and/or impact force to the overall operation and longevity of the CMUT may differ by region.

Figure 4:
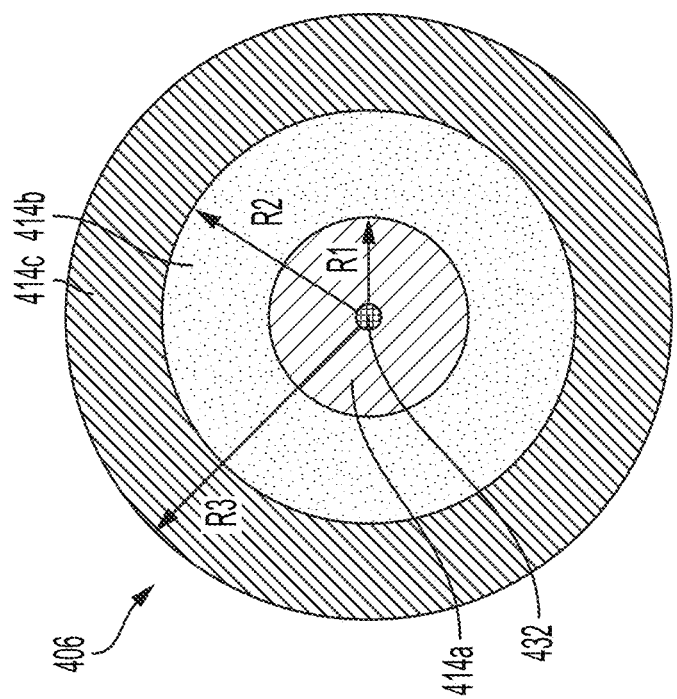
FIG. 4 illustrates a top view of three regions of a cavity bottom layer of a CMUT, in accordance with certain embodiments described herein.

FIG. 4 illustrates a top view of three regions of a cavity bottom layer 406 of a CMUT 600 (illustrated in FIG. 6), in accordance with certain embodiments described herein. The three regions are radially separated from each other. The cavity bottom layer 406 may be an example of the cavity bottom layer 306. The three regions include an inner region 414a, a middle region 414b, and an outer region 414c. In the example of FIG. 4, the inner region 414a is a circle or approximately a circle shape, centered at the centroid 432 of the cavity bottom layer 406, and having a radius $R_1$. The middle region 414b is an annular ring or approximately an annular ring in shape, centered at the centroid 432 of the cavity bottom layer 406, and having an inner radius $R_1$ and an outer radius $R_2$. The outer region 414c is an annular ring or approximately an annular ring in shape, centered at the centroid 432 of the cavity bottom layer 406, and having an inner radius $R_2$ and an outer radius $R_3$. Thus, $R_1$ is less than $R_2$ and $R_2$ is less than $R_3$.

Figure 5:
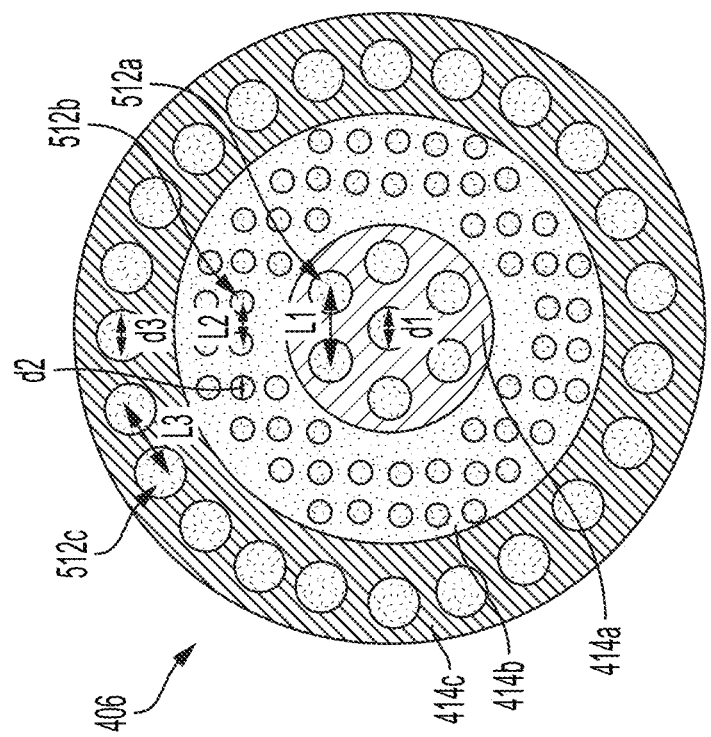
FIG. 5 illustrates a top view of non-uniform pedestals protruding from the three regions (the inner region, the middle region, and the outer region) of the cavity bottom layer of a CMUT, in accordance with certain embodiments described herein.

FIG. 5 illustrates a top view of non-uniform pedestals protruding from the three regions (the inner region 414a, the middle region 414b, and the outer region 414c) of the cavity bottom layer 406, in accordance with certain embodiments described herein. Inner pedestals 512a protrude from the cavity bottom layer 406 within the inner region 414a, middle pedestals 512b protrude from the cavity bottom layer 406 within the middle region 414b, and outer pedestals 512c protrude from the cavity bottom layer 406 within the outer region 414c. The inner pedestals 512a, the middle pedestals 512b, and the outer pedestals 512c may be examples of the non-uniform pedestals 312 of FIG. 3. The inner pedestals 512a, the middle pedestals 512b, and the outer pedestals 512c may be non-uniform in that at least one of the following is true: 1. The inner pedestals 512a have at least one characteristic different from that of the middle pedestals 512b; 2. The inner pedestals 512a have at least one characteristic different from that of the outer pedestals 512c; and 3. The middle pedestals 512b have at least one characteristic different than that of the outer pedestals 512c. As examples, the at least one characteristic may be top surface area, pitch, or both.

Figure 6:
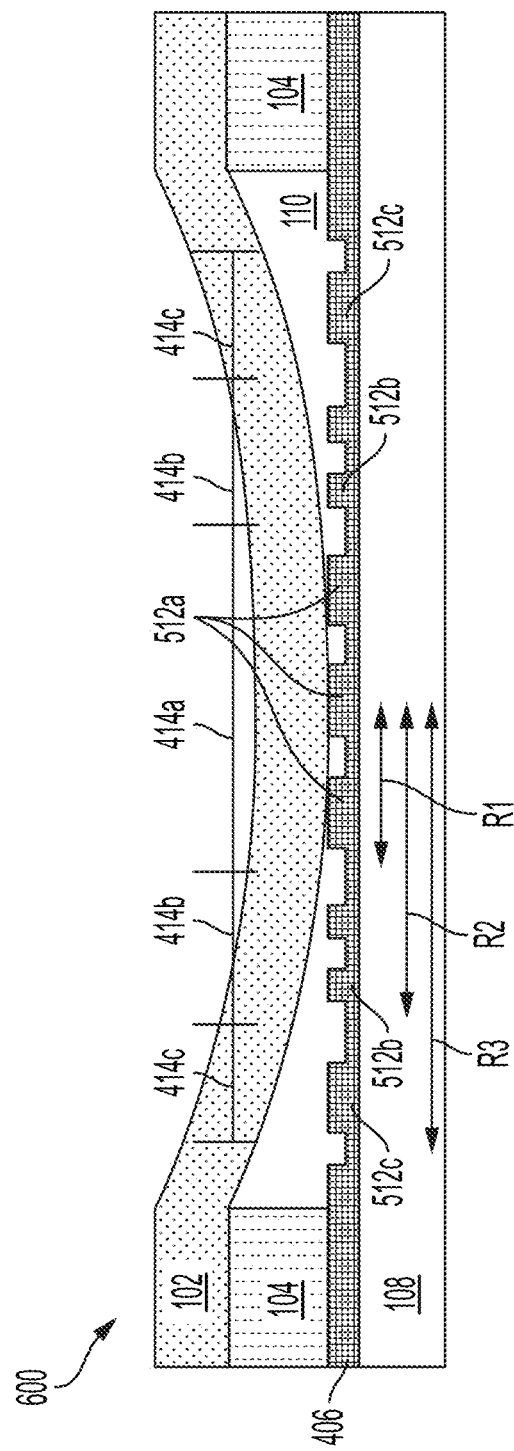
FIG. 6 illustrates a side view of a CMUT that includes the cavity bottom layer and the inner pedestals, the middle pedestals, and the outer pedestals.

In the specific example of FIG. 5, the inner pedestals 512a, the middle pedestals 512b, and the outer pedestals 512c are circular or approximately circular, such that the top surface area of a given pedestal having a diameter d may be equal to or approximately equal to $\pi d^2/4$. FIG. 5 labels the diameter of the inner pedestals 512a as $d_1$, the diameter of the middle pedestals 512b as $d_2$, and the diameter of the outer pedestals 512c as $d_3$. The top surface area of the inner pedestals 512a will be referred to as $SA_1 = \pi d_1^2/4$. The top surface area of the middle pedestals 512b will be referred to as $SA_2 = \pi d_2^2/4$. The top surface area of the outer pedestals 512c will be referred to as $SA_3 = \pi d_3^2/4$. FIG. 5 labels the pitch of the inner pedestals 512a as $L_1$, the pitch of the middle pedestals 512b as $L_2$, and the pitch of the outer pedestals 512c as $L_3$. Thus, in some embodiments, at least one of the following is true: 1. $SA_1$ and $SA_2$ are different; 2. $SA_1$ and $SA_3$ are different; 3. $SA_2$ and $SA_3$ are different; 4. $L_1$ and $L_2$ are different; 5. $L_1$ and $L_3$ are different; and 6. $L_2$ and $L_3$ are different. As described above, a particular value for a property of a set of pedestals (e.g., the diameter of a set of pedestals, the surface area of a set of pedestals, or the pitch of a set of pedestals) may refer to an average value of that property for each of the pedestals in the set. For example, $SA_1$ may be the average value of the top surface of each of the inner pedestals 512a, $d_1$ may be the average value of the diameter of each of the inner pedestals 512a, and $L_1$ may be the average value of the pitch of each adjacent pair of the inner pedestals 512a. FIG. 6 illustrates a side view of a CMUT 600 that includes the cavity bottom layer 406 and the inner pedestals 512a, the middle pedestals 512b, and the outer pedestals 512c.

The particular values for $d_1$, $d_2$, and $d_3$, and therefore the particular values for $SA_1$, $SA_2$, and $SA_3$, may depend on the specific characteristics of the CMUT 600. Without being bound by theory, in the examples of FIGS. 4-6, the inner region 414a may receive the strongest impact force from the membrane 102, because the movement of the membrane 102 may be largest towards the center of the CMUT 600. Thus, it may be helpful for the inner pedestals 512a in the inner region 414a to have a large top surface area $SA_1$, and therefore a large diameter $d_1$, in order to withstand this impact force from the membrane 102 and increase the longevity of the CMUT 600.

The outer region 414c is towards the edge of the CMUT 600, and thus it may receive less impact from the membrane 102 collapsing than the inner region 414a because there may be less movement of the membrane 102 in the outer region 414c and/or because the membrane 102 may not be able to physically contact the outer region 414c of the cavity bottom layer 406. However, instead of making the outer pedestals 512c in the outer region 512c have too small of a top surface area due to lack of need to withstand larger impact force, it may be helpful to make the outer pedestals 512c have a large top surface area due to the factor of CMUT sensing sensitivity. The edge area of the cavity 110 may contribute significantly to sensing sensitivity due to the large capacitance change at the edge of the CMUT 600 particularly when the device is working at collapse mode. This may mean that outer pedestals 512c having a small top surface area may result in decreased acoustic performance due to removal of more bottom dielectric material from the cavity bottom layer 406 (i.e., more air gaps between adjacent pedestals). Additionally, for anti-stiction considerations, the portion of the membrane 102 above the outer region 512c may have large restoring force due to the large contact angle between the membrane 102 and the cavity bottom layer 406. This, in turn, may make it less necessary to make the outer pedestals 512c have small top surface area for anti-stiction purposes. Thus, it may be helpful for the outer pedestals 512c in the outer region 414c to have a large top surface area $SA_3$, and therefore a large diameter $d_3$.

The middle region 414b may have less restoring force than the outer region 414c. Thus, it may be helpful for the middle pedestals 512b to have a smaller top surface area than the outer pedestals 512c to reduce stiction. The middle region 414b may also sustain less impact force from the membrane 102 than the inner region 414a. Thus, it may be helpful for the middle pedestals 512b not to have too small a top surface area, so that they can survive impact force from the membrane 102, but they may not need to have as large a top surface area as the inner pedestals 512c which may need to survive larger impact force. It may thus be helpful for the middle pedestals 512b to have a smaller top surface area $SA_2$, and therefore a smaller diameter $d_2$, than both the inner pedestals 512a and the outer pedestals 512c. In some embodiments, the inner pedestals 512a may have a smaller top surface area and diameter than the outer pedestals 512c. In some embodiments, the inner pedestals 512a may have a larger top surface area and diameter than the outer pedestals 512c. In some embodiments, the inner pedestals 512a may have the same or approximately the same top surface area and diameter as the outer pedestals 512c.

The particular values for $L_1$, $L_2$, and $L_3$ may also depend on the specific characteristics of the CMUT 600. Without being bound by theory, in the example of FIG. 6, stiction may be a more significant problem in the inner region 414a because collapse of the membrane 102 onto the cavity bottom layer 606 may occur most frequently towards the center of the CMUT 600. Thus, it may be helpful to increase the pitch $L_1$ in the inner region 414a so as to reduce the number of inner pedestals 512a and thereby reduce the top surface area of the inner region 414a for anti-stiction purposes. As described above, the middle pedestals 512b may be small in top surface area. However, sensing sensitivity may be significant in the middle region 414b. To increase the sensing sensitivity in the middle region 414b, it may be helpful to decrease the pitch $L_2$ so as to increase the number of middle pedestals 512b and thereby increase the top surface area of the middle region 414b for sensing sensitivity purposes. As also described above, sensing sensitivity may be significant in the outer region 414c. To increase the sensing sensitivity in the outer region 414c, it may be helpful to decrease the pitch $L_3$ so as to increase the number of outer pedestals 512c and thereby increase the top surface area of the outer region 414c for sensing sensitivity purposes. It may thus be helpful for the inner pedestals 512a to have a larger pitch $L_1$ than either the pitch $L_2$ of the middle pedestals 512b or the pitch $L_3$ of the outer pedestals 512c. In some embodiments, the pitch $L_2$ of the middle pedestals 512b may be larger than the pitch $L_3$ of the outer pedestals 512c. In some embodiments, the pitch $L_2$ of the middle pedestals 512b may be smaller than the pitch $L_3$ of the outer pedestals 512c. In some embodiments, the pitch $L_2$ of the middle pedestals 512b may be the same or approximately the same as the pitch $L_3$ of the outer pedestals 512c.

A non-limiting example of values of $R_1$, $R_2$, $R_3$, $d_1$, $d_2$, $d_3$, $L_1$, $L_2$, and $L_3$ as seen in FIGS. 4-6 is provided in Table 1.

TABLE 1

| Region 1 | Region 2 | Region 3 |
| --- | --- | --- |
| $R_1$ = 20 microns | $R_2$ = 40 microns | $R_3$ = 50 microns |
| $d_1$ = 3 microns | $d_2$ = 2 microns | $d_3$ = 4 microns |
| $L_1$ = 8 microns | $L_2$ = 6 microns | $L_3$ = 6 microns |

It should be appreciated that other values for the parameters listed in Table 1 may be provided. For example, $R_1$, $R_2$, and $R_3$ may assume any of the values shown for any of those parameters. Likewise, any of $d_1$, $d_2$, and $d_3$ may assume any of the values shown for any of those parameters. Any of $L_1$, $L_2$, and $L_3$ may assume any of the values shown for any of those parameters. Other values may be used for any of the listed parameters.

Figure 7:
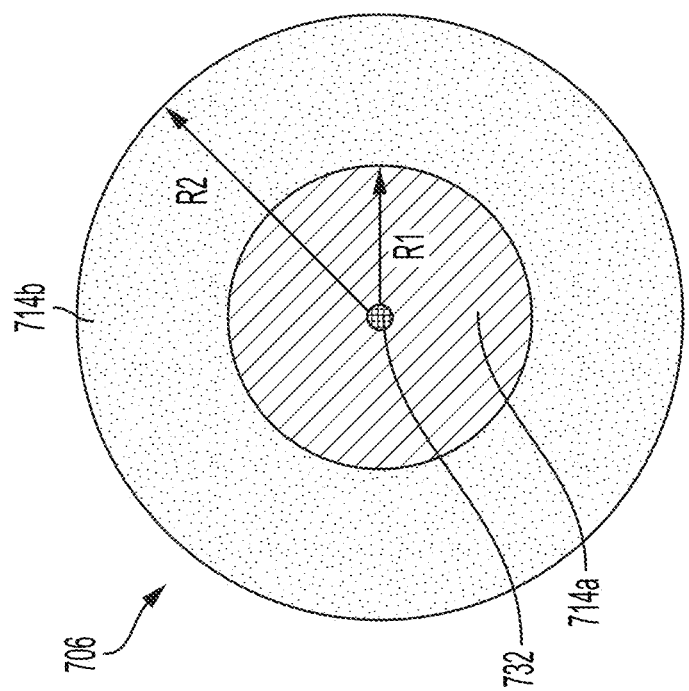
FIG. 7 illustrates a top view of two regions of a cavity bottom layer of a CMUT, in accordance with certain embodiments described herein.

FIG. 7 illustrates a top view of two regions of a cavity bottom layer 706 of a CMUT 900 (illustrated in FIG. 9), in accordance with certain embodiments described herein. The cavity bottom layer 706 may be an example of the cavity bottom layer 306. The two regions include an inner region 714a and an outer region 714b. In the example of FIG. 7, the inner region 714a is a circle or approximately a circle in shape, centered at the centroid 732 of the cavity bottom layer 706, and having a radius $R_1$. The outer region 714b is an annular ring or approximately an annular ring in shape, centered at the centroid 732 of the cavity bottom layer 706, and having an inner radius $R_1$ and an outer radius $R_2$. However, inner and outer regions of a cavity bottom layer may have different shapes than shown.

Figure 8:
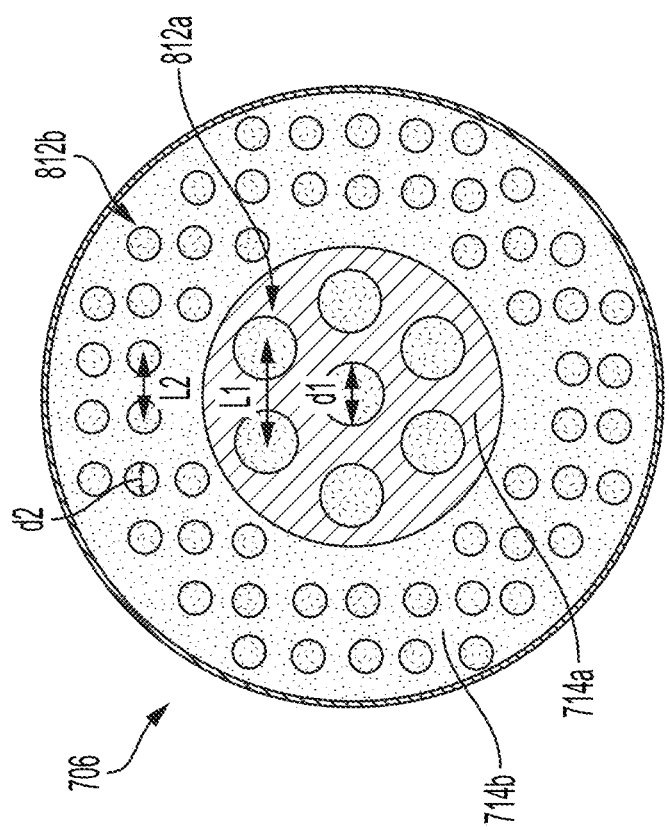
FIG. 8 illustrates a top view of non-uniform pedestals protruding from the two regions (the inner region and the outer region) of the cavity bottom layer, in accordance with certain embodiments described herein.

FIG. 8 illustrates a top view of non-uniform pedestals protruding from the two regions (the inner region 714a and the outer region 714b) of the cavity bottom layer 706, in accordance with certain embodiments described herein. Inner pedestals 812a protrude from the cavity bottom layer 706 within the inner region 714a and outer pedestals 812c protrude from the cavity bottom layer 706 within the outer region 714b. The inner pedestals 812a and the outer pedestals 812b may be examples of the non-uniform pedestals 312. The inner pedestals 812a and the outer pedestals 812b may be non-uniform in that the inner pedestals 812a have at least one characteristic different from that of the middle pedestals 812b. As examples, the at least one characteristic may be top surface area, pitch, or both.

Figure 9:
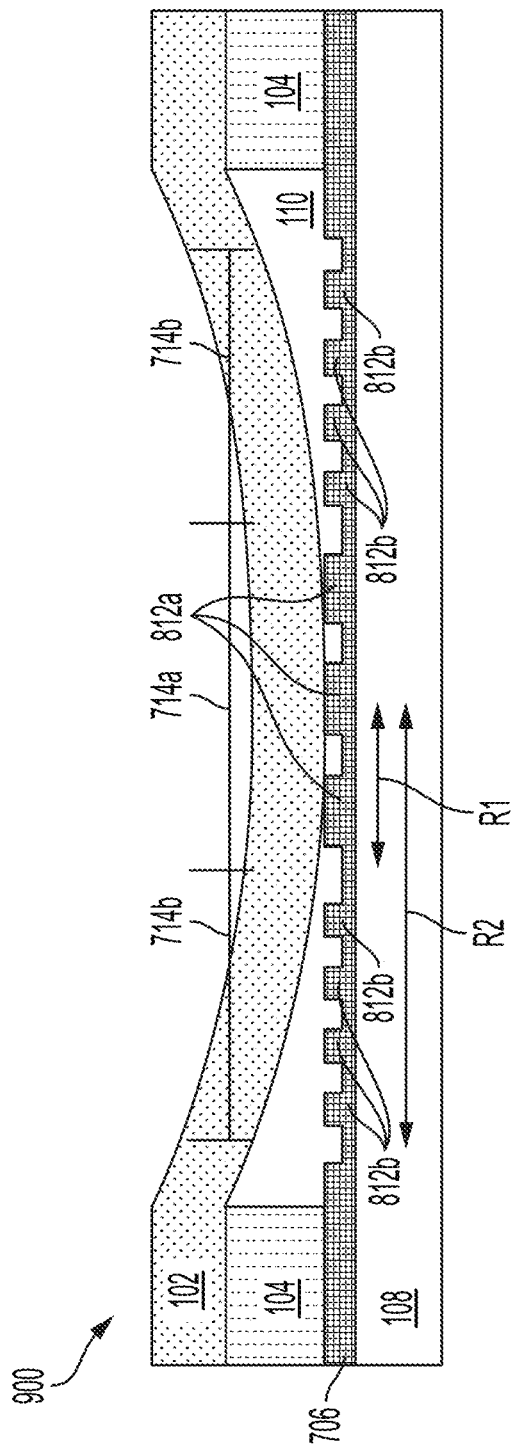
FIG. 9 illustrates a side view of a CMUT that includes the cavity bottom layer, the inner pedestals, and the outer pedestals.

In the specific example of FIG. 8, the inner pedestals 812a and the outer pedestals 812b are circular or approximately circular, such that the top surface area of a given pedestal having a diameter d may be equal to or approximately equal to $\pi d^2/4$. FIG. 8 labels the diameter of the inner pedestals 812a as $d_1$ and the diameter of the outer pedestals 812b as $d_2$. The top surface area of each of the inner pedestals 812a will be referred to as $SA_1 = \pi d_2^2/4$. The top surface area of each of the outer pedestals 812b will be referred to as $SA_2 = \pi d_2^2/4$. FIG. 8 labels the pitch of the inner pedestals 812a as $L_1$ and the pitch of the outer pedestals 812b as $L_2$. Thus, in some embodiments, at least one of the following is true: 1. $SA_1$ and $SA_2$ are different; and 2. $L_1$ and $L_2$ are different. As described above, a particular value for a property of a set of pedestals (e.g., the diameter of a set of pedestals, the surface area of a set of pedestals, or the pitch of a set of pedestals) may refer to an average value of that property for each of the pedestals in the set. For example, $SA_1$ may be the average value of the top surface of each of the inner pedestals 812a, $d_1$ may be the average value of the diameter of each of the inner pedestals 812a, and $L_1$ may be the average value of the pitch of each adjacent pair of the inner pedestals 812a. FIG. 9 illustrates a side view of a CMUT 900 that includes the cavity bottom layer 706, the inner pedestals 812a, and the outer pedestals 812b.

The particular values for $d_1$ and $d_2$ and therefore the particular values for $SA_1$ and $SA_2$, as well as the particular values for $L_1$ and $L_2$, may depend on the specific characteristics of the CMUT 900. For example, if the CMUT 900 has similar characteristics as the CMUT 600, such that considerations for the inner region 714a are similar to those of the inner region 414a and considerations for the outer region 714b are similar to those of the middle region 414b, it may be helpful for the outer pedestals 812b to have a smaller top surface area $SA_2$, and therefore a smaller diameter $d_2$, than the surface are $SA_1$ and the diameter $d_1$ of the inner pedestals 512a. Additionally, it may be helpful for the inner pedestals 812a to have a larger pitch $L_1$ than the pitch $L_2$ of the outer pedestals 812b.

In the specific examples of FIGS. 4-9, the pedestals are circular or approximately circular, such that the top surface area of a given pedestal having a diameter d may be equal to or approximately equal to $\pi d^2/4$. However, this application is not limited to circular pedestals, and in some embodiments, pedestals may have other shapes such as being oval, square, rectangular, or hexagonal, may not have a well-defined diameter, and/or the top surface area may not be equal to the expression given above for circular pedestals.

Some of the embodiments described herein include CMUTs described as having an inner region and an outer region, and some of the embodiments include CMUTs described as having an inner region, a middle region, and an outer region. Generally, a first set of pedestals may be considered to be in an inner region of a cavity bottom layer and a second set of pedestals may be considered to be in an outer region of the cavity bottom layer when the average value of the distance of each pedestal in the first group from the centroid of the cavity bottom layer is less than the average value of the distance of each pedestal in the second group from the centroid of the bottom surface of the cavity. Generally, a first set of pedestals may be considered to be in an inner region of a cavity bottom layer, a second set of pedestals may be considered to be in a middle region of the cavity bottom layer, and a third set of pedestals may be considered to be in an outer region of the cavity bottom layer, when the average value of the distance of each pedestal in the first group from the centroid of the cavity bottom layer is less than the average value of the distance of each pedestal in the second group from the centroid of the bottom surface of the cavity, and the average value of the distance of each pedestal in the second group from the centroid of the cavity bottom layer is less than the average value of the distance of each pedestal in the third group from the centroid of the bottom surface of the cavity. Additionally, while the examples in FIGS. 4-9 include two or three regions, some embodiments may include up to five regions.

The above description described how particular factors (such as stiction, impact force, and sensing sensitivity) relevant to the CMUTs 600 and 900 may mean that certain values for certain properties of certain pedestals may be preferable or optimal. However, it should be appreciated that this description is non-limiting, and different CMUTs may have different factors that may mean that different values may be preferable or optimal. For example, the above description described how in a three-region CMUT (such as the CMUT 600), it may be helpful for the middle pedestals to have smaller top surface areas than the outer pedestals and the inner pedestals. However, in some other CMUTs, it may be optimal for the middle pedestals to have larger top surface areas than the outer pedestals and/or the inner pedestals, based on the particular factors relevant to that CMUT. As another example, the above description described how in a two-region CMUT (such as the CMUT 900), it may be helpful for the outer pedestals to have smaller top surface areas than the inner pedestals. However, in some other CMUTs, it may be optimal for the outer pedestals to have larger top surface areas than the inner pedestals, based on the particular factors relevant to that CMUT. As another example, the above description described how in a three-region CMUT (such as the CMUT 600), it may be helpful for the inner pedestals to have a larger pitch than the middle pedestals or the outer pedestals. However, in some other CMUTs, it may be optimal for the inner pedestals to have a smaller pitch that the middle pedestals and/or the outer pedestals, based on the particular factors relevant to that CMUT. As another example, the above description described how in a two-region CMUT (such as the CMUT 900), it may be helpful for the inner pedestals to have a larger pitch than the outer pedestals. However, in some other CMUTs, it may be optimal for the inner pedestals to have a smaller pitch that the outer pedestals, based on the particular factors relevant to that CMUT.

Figure 10:
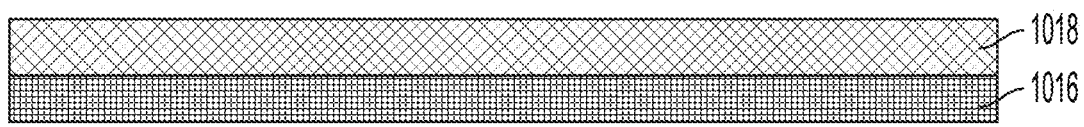
FIGS. 10-17 illustrate cross-sections of a CMUT fabrication sequence for fabricating a CMUT with non-uniform pedestals, in accordance with certain embodiments described herein.

FIGS. 10-17 illustrate cross-sections of a CMUT fabrication sequence for fabricating a CMUT with non-uniform pedestals, in accordance with certain embodiments described herein. FIG. 10 illustrates a substrate 1016 and a sensing metal layer 1018. The substrate 1016 and the sensing metal layer 1018 are in a vertical stack, with the sensing metal layer 1018 disposed on the substrate 1016. In some embodiments, the substrate 1016 may be a silicon substrate that includes integrated circuitry for ultrasound imaging. The substrate 1016 may further include one or more metal routing layers and vias (not illustrated) that electrically couple the integrated circuitry in the substrate 1016 to the sensing metal layer 1018. The sensing metal layer 1018 may include, for example, titanium and/or titanium nitride, and may be formed on the substrate 1016 using any suitable metal deposition process. In some embodiments, the integrated circuitry in the substrate 1016 may provide electrical signals to the sensing metal layer 1018 and receive and process electrical signals from the sensing metal layer 1018.

Figure 11:
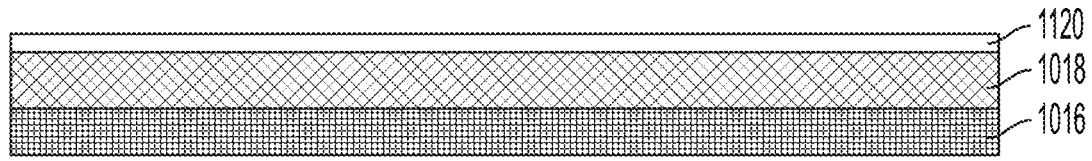

In FIG. 11, a layer 1120 is formed on the sensing metal layer 1018. The layer 1120 may include, for example, silicon dioxide, or any other suitable material for patterning. The layer 1120 may be, for example, 10-30 nm thick. The layer 1120 may be deposited on the sensing metal layer 1018 using any suitable process, such as chemical vapor deposition (CVD).

Figure 12:
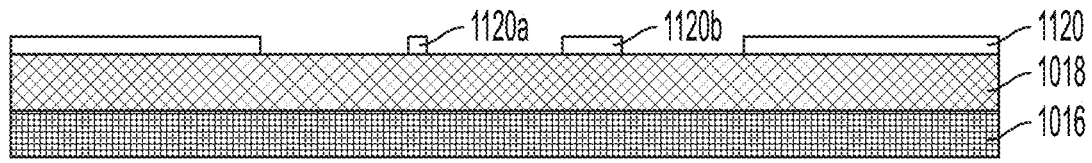

In FIG. 12, the layer 1120 is patterned. For example, the layer 1120 may be patterned using lithography and etching. The pattern of the layer 1120 may ultimately define the non-uniform pedestals, and thus in some embodiments such as the example in FIG. 12, different portions of the pattern of the layer 1120 may have different characteristics. For example, FIG. 12 illustrates two pedestal-shaped portions of the layer 1120 that may have different top surface areas and which may ultimately define pedestals (e.g., the pedestals 1712a and 1712b illustrated in FIG. 17) having different top surface areas.

Figure 13:
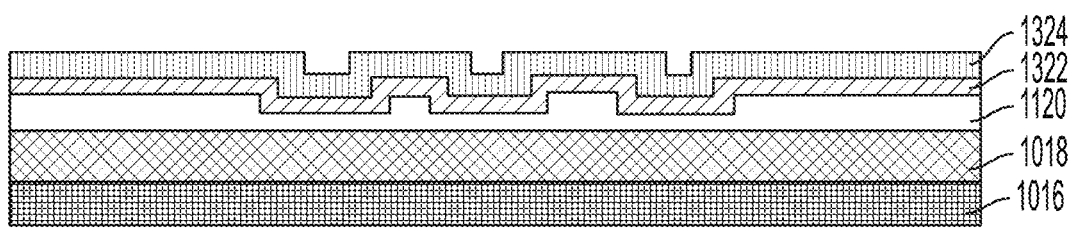

In FIG. 13, further material (e.g., 10-30 nm thick) of the same type as the layer 1120 is deposited on the layer 1120, a layer 1322 is deposited on the layer 1120, and a layer 1324 is deposited on the layer 1322. In some embodiments, the layer 1322 may include an insulating layer, such as an oxide, and in particular, the oxide may include aluminum oxide. In some embodiments, the layer 1322 may be any type of material that may reduce charging of a surface of the CMUT's cavity and/or may be capable of functioning as a stop layer. The layer 1322 may be deposited using any suitable process, such as atomic layer deposition (ALD). The layer 1322 may be, for example, 20-40 nm thick.

Portions of the layer 1322 deposited on patterned portions of the layer 1120 may ultimately be non-uniform pedestals of the CMUT. In the example of FIG. 13, portions of the layer 1322 deposited on the patterned portions 1120a and 1120b of the layer 1120 will become non-uniform pedestals 1712a and 1712b, which have at least one different characteristic (e.g., top surface area) from each other, based on the pattern of the layer 1120. The layer 1322 will ultimately become the cavity bottom layer of the CMUT. In some embodiments, the layer 1324 may include a material capable of functioning as a stop layer, such as a nitride, and in particular, the nitride may include silicon nitride. The layer 1324 may be, for example, 20-50 nm thick. The layer 1324 may be deposited using any suitable process, such as CVD. In some embodiments, instead of depositing more of the same material as the layer 1120 on the layer 1120, a different material may be deposited on the layer 1120.

Figure 14:
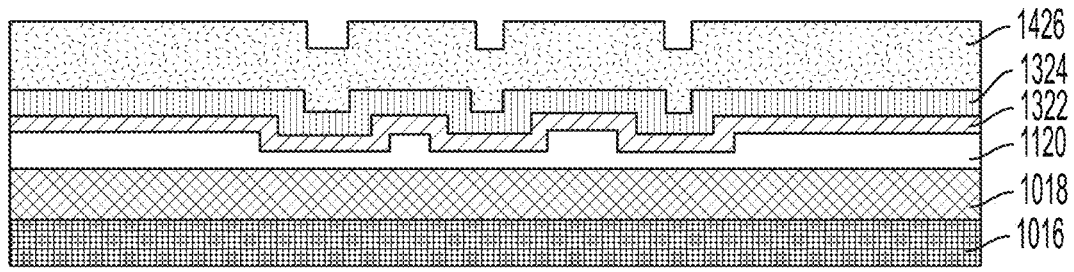

In FIG. 14, a layer 1426 is formed on the layer 1324. The layer 1426 may include, for example, silicon dioxide, or any other suitable material for patterning. The layer 1426 may be deposited on the layer 1324 using any suitable process, such as chemical vapor deposition (CVD). The layer 1426 may be, for example, 400-700 nm thick.

Figure 15:
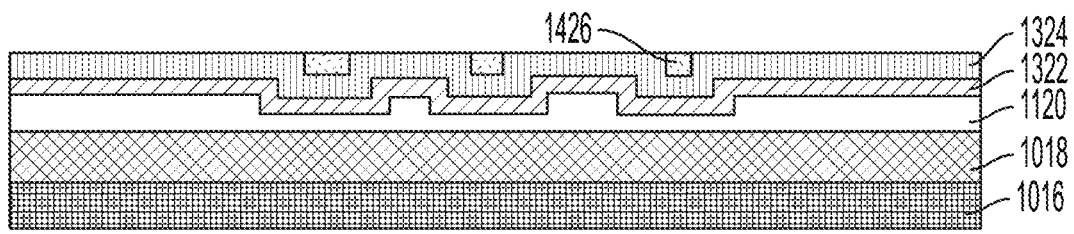

In FIG. 15, the layer 1426 is planarized. For example, the layer 1426 may be planarized using chemical-mechanical polishing (CMP). The layer 1324 may serve as a stop layer for the planarization.

Figure 16:
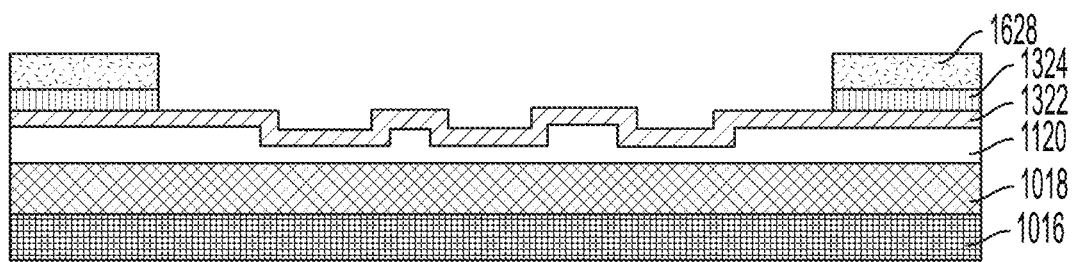

In FIG. 16, a layer 1628 is formed on the layer 1324 and the layers 1628 and 1324 are patterned (e.g., using photolithography and etching). The layer 1628 may include, for example, silicon dioxide, or any other suitable material for patterning. The layer 1628 may be deposited on the layer 1324 using any suitable process, such as chemical vapor deposition (CVD). The layer 1322 may serve as a stop layer for the etching. The layer 1628 may be, for example, 20-40 nm thick.

Figure 17:
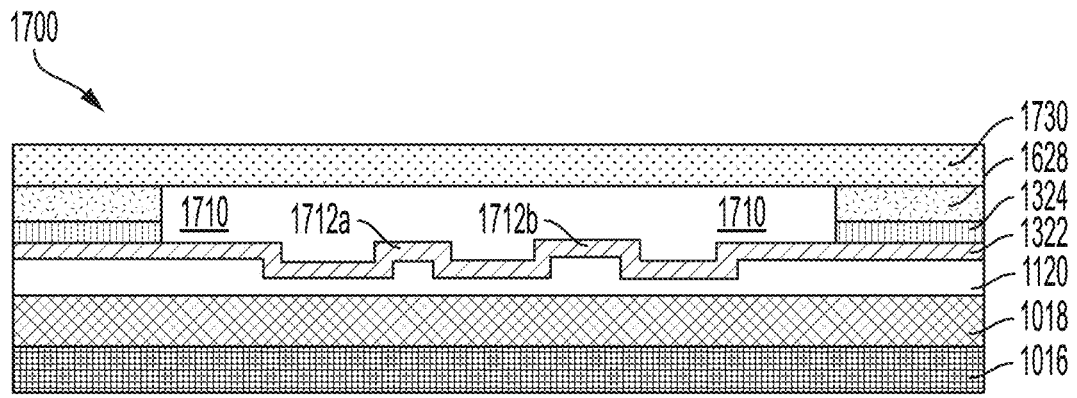

In FIG. 17, one or more layers 1730 are bonded to the layer 1628 to form a cavity 1710. The one or more layers 1730 may be layers on a different substrate and the one or more layers 1730 may be bonded to the layer 1628, after which the rest of the substrate on which the one or more layers 1730 were originally disposed may be removed. In some embodiments, the one or more layers 1730 may include an oxide layer (e.g., a silicon dioxide) disposed on silicon, where the oxide layer of the one or more layers 1730 may be adjacent to the cavity 1710.

The structure in FIG. 17 may be considered a CMUT 1700, and may be an example of any of the CMUTs described herein (e.g., the CMUTs 300, 600, and/or 900). The one or more layers 1730 may be any of the membranes described herein (e.g., the membrane) 102. The layers 1628 and 1324 may be examples of any of the sidewalls described herein (e.g., the sidewalls 104). The cavity 1710 may be an example of any of the cavities described herein (e.g., the cavity 110). The layer 1322 may be an example of the any of the cavity bottom layers described herein (e.g., the cavity bottom layers 306, 406, and/or 706). The layers 1120, 1018, and 1016 may together be an example of any of the substrates described herein (e.g., the substrate 108).

As illustrated in FIG. 17, non-illustrated pedestals 1712a and 1712b protrude from the layer 1322. As described above, the pattern of the layer 1120 may ultimately define the non-uniform pedestals 1712a and 1712b, and thus in some embodiments, different portions of the pattern of the layer 1120 may have different characteristics that may cause the pedestals 1712a and 1712b to have different characteristics. For example, the two pedestals 1712a and 1712b may have different top surface areas. It should be appreciated that other patterns in the layer 1120 may cause non-uniform pedestals to have other different characteristics. For example, the spacing between different patterned portions of the layer 1120 may cause different pedestals protruding from the layer 1322 to have different pitches.

While FIG. 17 illustrates the surfaces of the pedestals 1712a and 1712b including the same material as the surface of other portions of the layer 1322 from which pedestals do not protrude (i.e., the cavity bottom layer), in some embodiments the surfaces may include different materials. For example, there may be one or more extra additional fabrication steps in which one or more additional layers of material are formed on the pedestals 1712 and 1712b, one or more extra fabrication steps in which one or more additional layers of material are formed on other portions of the layer 1322 from which pedestals do not protrude, or both.

While FIG. 17 only illustrates two pedestals 1712a and 1712b for simplicity, it should be appreciated that the process illustrated in FIGS. 10-17 may be used to form a CMUT having more than two non-uniform pedestals. Further description of fabrication of a CMUT may be found in U.S. Pat. No. 9,067,779 titled "MICROFABRICATED ULTRASONIC TRANSDUCERS AND RELATED APPARATUS AND METHODS," issued on Jun. 30, 2015 (and assigned to the assignee of the instant application), the content of which is incorporated by reference herein in its entirety; and U.S. Patent Publication No. 2019/0275561 A1 titled "ULTRASOUND TRANSDUCER DEVICES AND METHODS FOR FABRICATING ULTRASOUND TRANSDUCER DEVICES," published on Sep. 12, 2019 (and assigned to the assignee of the instant application), the content of which is incorporated by reference herein in its entirety.

Figure 18:
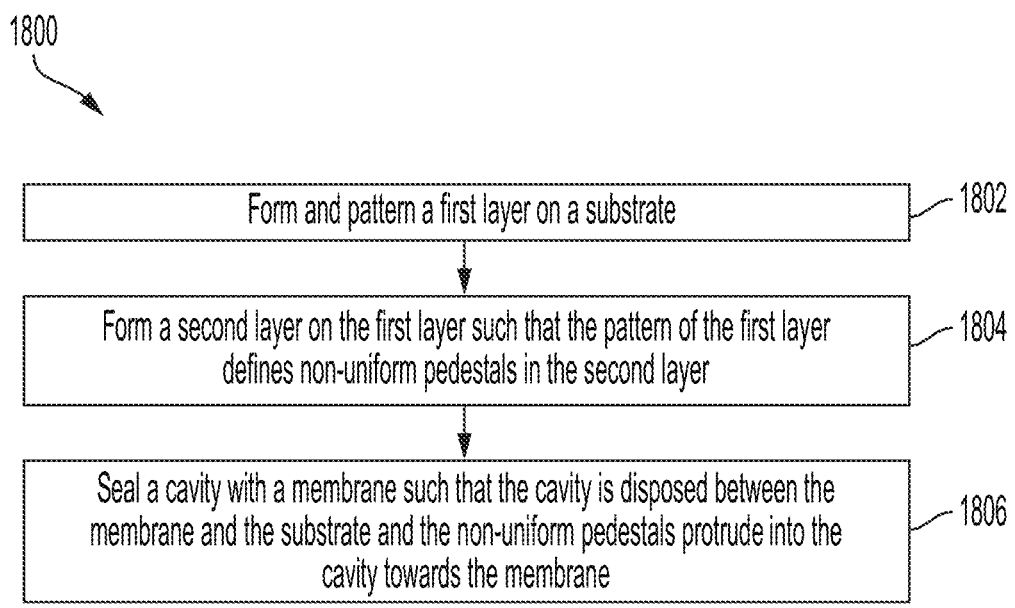
FIG. 18 illustrates a process for fabricating a CMUT having non-uniform pedestals.

FIG. 18 illustrates a process 1800 for fabricating a CMUT having non-uniform pedestals. In act 1802, a first layer (e.g., the layer 1120) is formed and patterned on a substrate (e.g., the substrate 1016 and the sensing metal layer 1018). Further description of act 1802 may be found with reference to FIGS. 10-12. In act 1804, a second layer (e.g., the layer 1322) is formed on the first layer such that the pattern of the first layer defines non-uniform pedestals (e.g., the non-uniform pedestals 1712a and 1712b) in the second layer. Further description of act 1804 may be found with reference to FIGS. 13-16. In act 1806, a cavity (e.g., the cavity 1710) is sealed with a membrane (e.g., the one or more layers 1730) such that the cavity is disposed between the membrane and the substrate and the non-uniform pedestals protrude into the cavity towards the membrane. Further description of act 1806 may be found with reference to FIG. 17.

Figure 19:
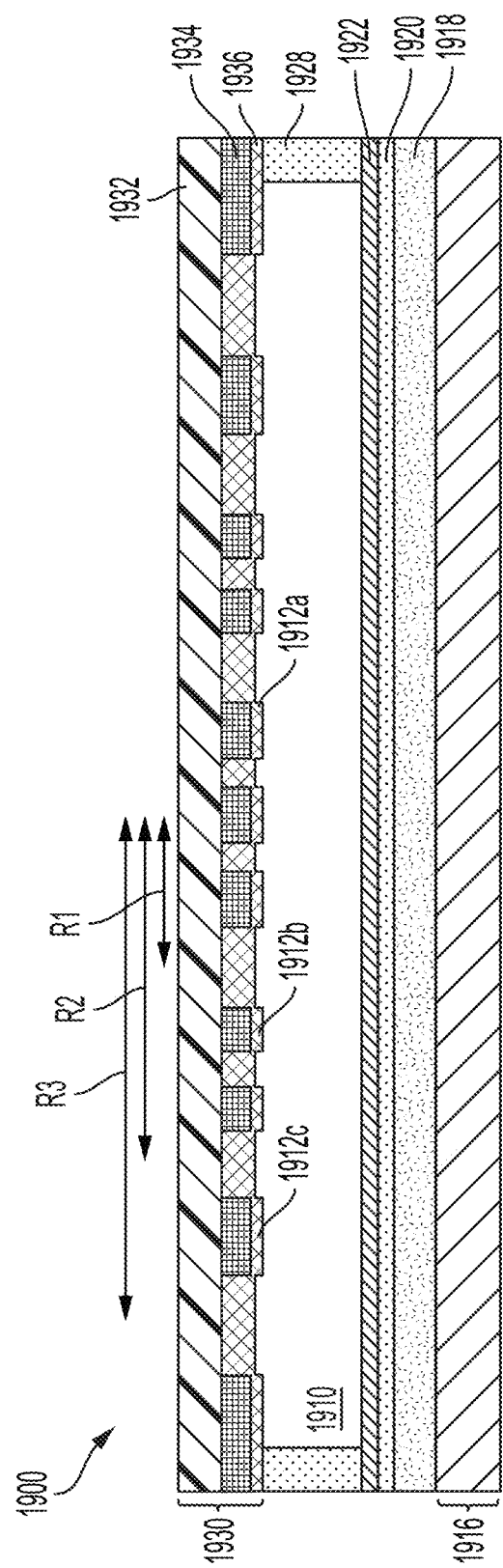
FIG. 19 illustrates a cross-sectional view of a CMUT including non-uniform pedestals protruding from the membrane, in accordance with certain embodiments described herein.

FIG. 19 illustrates a cross-sectional view of a CMUT 1900 including non-uniform pedestals protruding from the membrane 1930, in accordance with certain embodiments described herein. The membrane 1930 is bonded to the sidewalls 1928 to form a cavity 1910. The membrane 1930 includes a substrate 1932 and a first oxide layer 1934 and a second oxide layer 1936 bonded to the substrate 1932. After the membrane 1930 is bonded to the sidewalls 1928, a portion of the thickness of the substrate 1932 may be removed (e.g., by chemical-mechanical polishing or other thinning technique). In some embodiments, the first and second oxide layers 1934, 1936 may be formed of silicon dioxide and may be disposed on the substrate 1930, which may be a silicon substrate.

Portions of the first oxide layer 1934 and second oxide layer 1936 deposited on the substrate 1932 may ultimately be non-uniform pedestals 1912a, 1912b, and/or 1912c of the CMUT 1900. In the example of FIG. 19, after deposition of the first oxide layer 1934, the first oxide layer 1934 may be patterned (e.g., by lithography followed by etching) to define the non-uniform pedestals 1912a, 1912b, and/or 1912c. Portions of the layer 1936 deposited on the patterned portions of first oxide layer 1934 will become non-uniform pedestals 1912a, 1912b, and 1712c, which have at least one different characteristic (e.g., top surface area) from each other, based on the pattern of the layer 1934.

In some embodiments, the non-uniform pedestals 1912a, 1912b, and 1912c may be disposed in three regions that are radially separated from each other (e.g., as described in connection with FIGS. 4 and 5 herein). In the example of FIG. 19, the three regions may include an inner region having a radius $R_1$, a middle region 414b having an inner radius $R_1$ and an outer radius $R_2$, and an outer region having an inner radius $R_2$ and an outer radius $R_3$. Thus, $R_1$ is less than $R_2$ and $R_2$ is less than $R_3$.

The non-uniform pedestals 1912a, 1912b, and 1912c include inner pedestals 1912a, middle pedestals 1912b, and outer pedestals 1912c. Inner pedestals 1912a protrude from the membrane 1930 within the inner region, middle pedestals 1912b protrude from the membrane 1930 within the middle region, and outer pedestals 1912c protrude from the membrane 1930 within the outer region. The inner pedestals 1912a, the middle pedestals 1912b, and the outer pedestals 1912c may be non-uniform in the same ways that the inner pedestals 512a, the middle pedestals 512b, and the outer pedestals 512c are non-uniform, as described in connection with FIG. 5 herein. For example, at least one of the following may be true: 1. The inner pedestals 1912a have at least one characteristic different from that of the middle pedestals 1912b; 2. The inner pedestals 1912a have at least one characteristic different from that of the outer pedestals 1912c; and 3. The middle pedestals 1912b have at least one characteristic different than that of the outer pedestals 1912c. As examples, the at least one characteristic may be top surface area, pitch, or both.

The bottom surface of the CMUT 1900 is formed on a substrate 1916 and includes a metal sensing layer 1918, an oxide layer 1920, and an optional passivation layer 1922. In some embodiments, the substrate 1916 may be a silicon substrate that includes integrated circuitry for ultrasound imaging. The substrate 1916 may further include one or more metal routing layers and vias (not illustrated) that electrically couple the integrated circuitry in the substrate 1916 to the sensing metal layer 1918. The sensing metal layer 1918 may include, for example, titanium and/or titanium nitride, and may be formed on the substrate 1916 using any suitable metal deposition process. In some embodiments, the integrated circuitry in the substrate 1916 may provide electrical signals to the sensing metal layer 1918 and receive and process electrical signals from the sensing metal layer 1918.

The oxide layer 1920 is formed on the sensing metal layer 1918. The layer 1920 may include, for example, silicon dioxide. The layer 1920 may be, for example, 10-30 nm thick. The layer 1920 may be deposited on the sensing metal layer 1918 using, for example, chemical vapor deposition (CVD).

The optional passivation layer 1922 is deposited on the oxide layer 1920. In some embodiments, the passivation layer 1922 may include an insulating layer, such as an oxide, and in particular, the oxide may include aluminum oxide. The passivation layer 1922 may be deposited using, for example, atomic layer deposition (ALD). The passivation layer 1922 may be, for example, 20-40 nm thick.

The cavity 1910 is formed between substrate 1916 and membrane 1930 with a perimeter defined by sidewalls 1928. Sidewalls 1928 are formed on passivation layer 1922 and/or oxide layer 1920, if optional passivation layer 1922 is omitted. The sidewalls 1928 may be deposited on the layer 1922 and/or 1920 using, for example, chemical vapor deposition (CVD). The layer 1928 may be, for example, 400-700 nm thick.

In some embodiments, the CMUTs described herein (e.g., CMUT 300, 600, 900, 1700, and/or 1900) may be integrated into an ultrasound device. For example, the CMUTs may be arranged to form an array. In some embodiments, the CMUTs form a 2D array, although in alternative embodiments the CMUTs may form a 1.5D array or a 1D array. The array includes hundreds or thousands of CMUTs in some embodiments. For example, the ultrasound device in some embodiments includes an array of between 7,000 and 12,000 (e.g., 9,000) ultrasonic transducers arranged in a 2D array. Other numbers of ultrasonic transducers may be implemented in alternative embodiments.

In some embodiments, the CMUTs described herein (e.g., CMUT 300, 600, 900, 1700, and/or 1900) may be integrated into a point-of-care ultrasound device. For example, the ultrasound device may be a handheld ultrasound probe or a patch. Additional aspects of a handheld ultrasound device are described in U.S. patent Application Publication No.: 2017/0360399 titled "Universal Ultrasound Device and Related Apparatus and Methods," filed on Jun. 19, 2017, which is incorporated herein by reference in its entirety.

The indefinite articles "a" and "an," as used herein in the specification and in the claims, unless clearly indicated to the contrary, should be understood to mean "at least one."

The phrase "and/or," as used herein in the specification and in the claims, should be understood to mean "either or both" of the elements so conjoined, i.e., elements that are conjunctively present in some cases and disjunctively present in other cases. Multiple elements listed with "and/or" should be construed in the same fashion, i.e., "one or more" of the elements so conjoined. Other elements may optionally be present other than the elements specifically identified by the "and/or" clause, whether related or unrelated to those elements specifically identified.

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified.

Use of ordinal terms such as "first," "second," "third," etc., in the claims to modify a claim element does not by itself connote any priority, precedence, or order of one claim element over another or the temporal order in which acts of a method are performed, but are used merely as labels to distinguish one claim element having a certain name from another element having a same name (but for use of the ordinal term) to distinguish the claim elements.

As used herein, reference to a numerical value being between two endpoints should be understood to encompass the situation in which the numerical value can assume either of the endpoints. For example, stating that a characteristic has a value between A and B, or between approximately A and B, should be understood to mean that the indicated range is inclusive of the endpoints A and B unless otherwise noted.

In the claims, as well as in the specification above, all transitional phrases such as "comprising," "including," "carrying," "having," "containing," "involving," "holding," "composed of," and the like are to be understood to be open-ended, i.e., to mean including but not limited to. Only the transitional phrases "consisting of" and "consisting essentially of" shall be closed or semi-closed transitional phrases, respectively.

Having described above several aspects of at least one embodiment, it is to be appreciated various alterations, modifications, and improvements will readily occur to those skilled in the art.

Such alterations, modifications, and improvements are intended to be object of this disclosure. Accordingly, the foregoing description and drawings are by way of example only.

What is claimed is:

1. An ultrasound device, comprising:
a capacitive micromachined ultrasonic transducer (CMUT), comprising:
a substrate;
a membrane coupled to the substrate such that a cavity exists between the substrate and the membrane;
a cavity bottom layer adjacent to the substrate; and
non-uniform pedestals protruding from the cavity bottom layer into the cavity and towards the membrane, wherein the non-uniform pedestals comprise first non-uniform pedestals having a first pedestal diameter, d1, and second non-uniform pedestals having a second pedestal diameter, $d_2$, different than $d_1$, and
the cavity bottom layer comprises:
a first region having a first radius, the first region comprising the first nonuniform pedestals; and
a second region having a first inner radius and a first outer radius, the first inner radius being approximately equal to the first radius and the first outer radius being greater than the first inner radius, the second region comprising the second non-uniform pedestals.

2. The ultrasound device of claim 1, wherein $d_1$ is greater than $d_2$.

3. The ultrasound device of claim 1, wherein:
each adjacent pair of the first non-uniform pedestals has a pitch, $L_1$,
each adjacent pair of the second non-uniform pedestals has a pitch, $L_2$, and $L_1$ has a different value than $L_2$.

4. The ultrasound device of claim 3, wherein $L_1$ is greater than $L_2$.

5. The ultrasound device of claim 1, wherein:
the non-uniform pedestals further comprise third non-uniform pedestals having a third pedestal diameter, $d_3$, and
the cavity bottom layer further comprises a third region having a second inner radius and a second outer radius, the second inner radius being approximately equal to the first outer radius and the second outer radius being greater than the second inner radius, the second region comprising the third non-uniform pedestals.

6. The ultrasound device of claim 5, wherein $d_3$ has a different value than $d_1$ and $d_2$.

7. The ultrasound device of claim 6, wherein $d_3$ is greater than $d_2$ and less than $d_1$.

8. The ultrasound device of claim 5, wherein each adjacent pair of the third non-uniform pedestals has a pitch $L_3$, and
L3 has a different value than $L_1$ and $L_2$.

9. The ultrasound device of claim 8, wherein $L_1$ is greater than $L_3$.

10. The ultrasound device of claim 9, wherein $L_2$ is greater than or approximately equal to $L_3$.

11. The ultrasound device of claim 1, wherein each of the non-uniform pedestals has a height that is in a range from 20 nanometers to 100 nanometers above the bottom surface of the cavity.

* * * * *